United States Patent
Oba et al.

(10) Patent No.: US 10,761,048 B2
(45) Date of Patent: Sep. 1, 2020

(54) METAL TERMINAL FOR GAS SENSOR, GAS SENSOR AND METHOD FOR MANUFACTURING GAS SENSOR

(71) Applicant: NGK Spark Plug Co., LTD., Nagoya (JP)

(72) Inventors: Takehiro Oba, Kounan (JP); Shogo Nagata, Komaki (JP); Shunya Mihara, Komaki (JP)

(73) Assignee: NGK Spark Plug Co., LTD., Nagoya (JP)

( * ) Notice: Subject to any disclaimer, the term of this patent is extended or adjusted under 35 U.S.C. 154(b) by 282 days.

(21) Appl. No.: 15/643,090

(22) Filed: Jul. 6, 2017

(65) Prior Publication Data

US 2018/0011049 A1 Jan. 11, 2018

(30) Foreign Application Priority Data

Jul. 7, 2016 (JP) .................................. 2016-134989
Jun. 30, 2017 (JP) .................................. 2017-129059

(51) Int. Cl.
| | |
|---|---|
| G01N 27/406 | (2006.01) |
| G01N 27/407 | (2006.01) |
| G01N 33/00 | (2006.01) |
| H01R 11/18 | (2006.01) |
| H01R 11/28 | (2006.01) |

(52) U.S. Cl.
CPC ..... *G01N 27/4062* (2013.01); *G01N 27/4067* (2013.01); *G01N 27/4074* (2013.01); *G01N 27/4075* (2013.01); *G01N 27/4077* (2013.01); *G01N 33/0037* (2013.01); *H01R 11/18* (2013.01); *H01R 11/28* (2013.01); *Y02A 50/245* (2018.01)

(58) Field of Classification Search
CPC ........... G01N 27/4062; G01N 27/4077; G01N 27/4067; G01N 27/4074; G01N 27/4075; H01R 11/28; H01R 11/18; Y02A 50/245
See application file for complete search history.

(56) References Cited

U.S. PATENT DOCUMENTS 6,463,788 B2 * 10/2002 Nakano .............. G01N 27/4062
204/424
2014/0020446 A1 * 1/2014 Yonezu .............. G01N 33/0009
73/23.2

FOREIGN PATENT DOCUMENTS

JP 2002-323470 A 11/2002

* cited by examiner

*Primary Examiner* — Louis J Rufo
(74) *Attorney, Agent, or Firm* — Leason Ellis LLP

(57) ABSTRACT

A metal terminal includes a front-side terminal member and a rear-side terminal member. The front-side terminal member includes a female connection portion, and the rear-side terminal member includes a male connection portion. The female connection portion has an insertion port in which the male connection portion is inserted. The insertion port is formed in a shape that prevents the insertion port and the male connection portion from coming into contact with each other when the male connection portion is inserted therein. The female connection portion includes a terminal contact portion which brings the male connection portion and the female connection portion into contact with each other by pressing the male connection portion toward the female connection portion inside the female connection portion.

11 Claims, 13 Drawing Sheets

METAL TERMINAL FOR GAS SENSOR, GAS SENSOR AND METHOD FOR MANUFACTURING GAS SENSOR

This application claims the benefit of Japanese Patent Applications No. 2016-134989, filed Jul. 7, 2016 and No. 2017-129059, filed Jun. 30, 2017, both of which are incorporated herein by reference in their entireties

FIELD OF THE INVENTION

The present disclosure relates to a metal terminal used for a gas sensor that includes a sensor element having an electrode terminal portion, and a signal line for outputting a detection signal to the outside.

BACKGROUND OF THE INVENTION

A gas sensor for detecting a specific component contained in a gas to be measured includes, for example, a sensor element having an electrode terminal portion, a metal terminal electrically connected to the electrode terminal portion of the sensor element, and a signal line that is electrically connected to the metal terminal and forms a signal path for outputting a detection signal to the outside.

The metal terminal of the gas sensor as described above is not limited to one composed of a single member, and a metal terminal composed of a male terminal member and a female terminal member being connected to each other has been proposed as described in Japanese Patent Application Laid-Open (kokai) No. 2002-323470.

Problems to be Solved by the Invention

However, when a work for fitting the male terminal member to the female terminal member is performed, the outer peripheral surface of the male terminal member and the inner peripheral surface of the female terminal member may come into contact with each other, which may cause deterioration in efficiency of the fitting work. Further, when the male terminal member and the female terminal member, which are fitted to each other, are fixed by welding, a gap may be formed at a contact portion between the male terminal member and the female terminal member, which may cause welding failure.

An object of the present disclosure is to improve work efficiency and welding stability.

SUMMARY OF THE INVENTION

Means for Solving the Problems

One aspect of the present disclosure is a metal terminal for a gas sensor, which is used for a gas sensor including: a sensor element having an electrode terminal portion; and a signal line. The electrode terminal portion outputs a detection signal indicating a result of detection of a detection target gas to the outside. The signal line forms a signal path for outputting the detection signal to the outside. The metal terminal for the gas sensor according to the present disclosure is electrically connected to the electrode terminal portion and the signal line, to transmit the detection signal from the electrode terminal portion to the signal line.

The metal terminal for the gas sensor according to the present disclosure includes a front-side terminal member that contacts the electrode terminal portion, and a rear-side terminal member that is connected to the signal line. The front-side terminal member includes a front-side connection portion via which the front-side terminal member is connected to the rear-side terminal member. The rear-side terminal member includes a rear-side connection portion via which the rear-side terminal member is connected to the front-side terminal member.

The front-side connection portion is a female connection portion or a male connection portion. The rear-side connection portion is the male connection portion when the front-side connection portion is the female connection portion, and is the female connection portion when the front-side connection portion is the male connection portion.

The female connection portion has an insertion port in which the male connection portion is inserted. The insertion port is formed in a shape that prevents the insertion port and the male connection portion from coming into contact with each other when the male connection portion is inserted into the female connection portion through the insertion port.

Either the female connection portion or the male connection portion includes a terminal contact portion configured to bring the male connection portion and the female connection portion into contact with each other inside the female connection portion by pressing the male connection portion toward the female connection portion, when the male connection portion is inserted into the female connection portion.

In the metal terminal for the gas sensor according to the present disclosure configured as described above, the insertion port of the female connection portion is formed in a shape that prevents the insertion port and the male connection portion from coming into contact with each other when the male connection portion is inserted therein. Therefore, the metal terminal for the gas sensor according to the present disclosure can inhibit occurrence of a situation that, when the male connection portion is inserted into the female connection portion, the insertion work is interfered by contact of the female connection portion and the male connection portion. Thus, efficiency of the work for connecting the female connection portion and the male connection portion can be improved.

In the metal terminal for the gas sensor according to the present disclosure, the terminal contact portion brings the male connection portion and the female connection portion into contact with each other by pressing the male connection portion toward the female connection portion inside the female connection portion, when the male connection portion is inserted into the female connection portion. Thereby, the metal terminal for the gas sensor according to the present disclosure can hold the state where the male connection portion and the female connection portion are in contact with each other after the male connection portion is inserted into the female connection portion. Therefore, welding can be performed at the position where the male connection portion and the female connection portion are in contact with each other. Thus, the metal terminal for the gas sensor according to the present disclosure inhibits occurrence of a situation that a gap is formed at a welding point at which the female connection portion and the male connection portion are fixed to each other by welding, thereby improving stability of welding.

In the aspect of the present disclosure, at least two terminal contact portions may be provided along a direction perpendicular to an insertion direction in which the male connection portion is inserted into the female connection portion.

In the metal terminal for the gas sensor according to the present disclosure configured as described above, movement of the male connection portion along the direction perpendicular to the insertion direction can be restricted inside the female connection portion, thereby improving stability of the position of the male connection portion inside the female connection portion.

In the aspect of the present disclosure, at least two terminal contact portions may be provided along the insertion direction in which the male connection portion is inserted into the female connection portion.

In the metal terminal for the gas sensor according to the present disclosure configured as described above, movement of the male connection portion along the insertion direction can be restricted inside the female connection portion, thereby improving stability of the position of the male connection portion inside the female connection portion.

In the aspect of the present disclosure, the front-side connection portion may include the terminal contact portion.

In the metal terminal for the gas sensor according to the present disclosure configured as described above, a material capable of maintaining elasticity even after being repeatedly exposed to high temperature is frequently used as a material of the front-side terminal member in order to maintain the contact with the electrode terminal portion by the front-side terminal member. Therefore, in the metal terminal for the gas sensor according to the present disclosure, since the front-side connection portion has the terminal contact portion, the terminal contact portion can also be formed from the material capable of maintaining elasticity even after being repeatedly exposed to high temperature. Thus, the metal terminal for the gas sensor according to the present disclosure can inhibit deterioration in the function of bringing the male connection portion and the female connection portion into contact with each other by pressing the male connection portion.

Another aspect of the present disclosure is a gas sensor including: a sensor element having an electrode terminal portion; a metal terminal electrically connected to the electrode terminal portion of the sensor element; and a signal line electrically connected to the metal terminal for forming a signal path for outputting a detection signal to the outside.

In the gas sensor according to the present disclosure, the metal terminal includes a front-side terminal member that contacts the electrode terminal portion, and a rear-side terminal member that is connected to the signal line. The front-side terminal member includes a front-side connection portion via which the front-side terminal member is connected to the rear-side terminal member. The rear-side terminal member includes a rear-side connection portion via which the rear-side terminal member is connected to the front-side terminal member.

The front-side connection portion is a female connection portion or a male connection portion. The rear-side connection portion is the male connection portion when the front-side connection portion is the female connection portion, and is the female connection portion when the front-side connection portion is the male connection portion.

The female connection portion has an insertion port in which the male connection portion is inserted. The insertion port is formed in a shape that prevents the insertion port and the male connection portion from coming into contact with each other when the male connection portion is inserted into the female connection portion through the insertion port.

Either the female connection portion or the male connection portion includes a terminal contact portion configured to bring the male connection portion and the female connection portion into contact with each other inside the female connection portion by pressing the male connection portion toward the female connection portion, when the male connection portion is inserted into the female connection portion The gas sensor according to the present disclosure configured as described above is a gas sensor including the metal terminal for the gas sensor according to the aforementioned aspect of the present disclosure, and therefore, can achieve the same effects as those of the metal terminal for the gas sensor according to the present disclosure.

In the other aspect of the present disclosure, the male connection portion and the female connection portion may be welded together at a contact portion between the male connection portion and the female connection portion. Thereby, the gas sensor according to the present disclosure inhibits occurrence of a situation that a gap is formed at a welding point at which the female connection portion and the male connection portion are fixed to each other by welding, thereby improving stability of welding.

In the other aspect of the present disclosure, the gas sensor comprises a contact point at which the terminal contact portion is in contact with either the female connection portion or the male connection portion and a welding point at which the female connection portion and the male connection portion are welded together. The contact point and the welding point may be located on the same plane perpendicular to the insertion direction in which the male connection portion is inserted into the female connection portion.

In the gas sensor according to the present disclosure configured as described above, since the terminal contact portion presses the male connection portion toward the female connection portion near the welding point, contact of the female connection portion and the male connection portion at the welding point can be made stronger, thereby further improving stability of welding.

In the other aspect of the present disclosure, at least two terminal contact portions may be provided along the insertion direction in which the male connection portion is inserted into the female connection portion. In the other aspect of the present disclosure, further, a first contact point at which the first terminal contact portion is in contact with either the female connection portion or the male connection portion and a second contact point at which the second terminal contact portion is in contact with either the female connection portion or the male connection portion may be located on opposite sides from each other with a welding plane therebetween. The first terminal contact portion is one terminal contact portion among the at least two terminal contact portions. The second terminal contact portion is one terminal contact portion other than the first terminal contact portion among the at least two terminal contact portions. The welding plane is a plane that is perpendicular to the insertion direction in which the male connection portion is inserted into the female connection portion, and that passes a welding point at which the female connection portion and the male connection portion are welded together.

In the gas sensor according to the present disclosure configured as described above, since the state where the female connection portion and the male connection portion are in contact with each other is maintained by the first terminal contact portion and the second terminal contact portion which are located on the opposite sides with the welding plane therebetween, the contact of the female connection portion and the male connection portion at the welding point can be made stronger, thereby further improving stability of welding.

Still another aspect of the present disclosure is a method for producing a gas sensor including a sensor element, a metal terminal, a separator, and a signal line. The separator holds the metal terminal in a state of surrounding the metal terminal. The separator includes a front-side separator configured to hold the front-side terminal member in a state of surrounding the front-side terminal member, and a rear-side separator configured to hold the rear-side terminal member in a state of surrounding the rear-side terminal member.

The method for producing the gas sensor according to the present disclosure includes a front-side insertion step, a rear-side insertion step, and a fitting step.

In the front-side insertion step, the front-side terminal member is inserted into the front-side separator, with the front-side connection portion of the front-side terminal member being positioned at the rear side of the front-side separator.

In the rear-side insertion step, the rear-side terminal member is inserted into the rear-side separator, with the rear-side connection portion of the rear-side terminal member being positioned at the front side of the rear-side separator.

In the fitting step, a rear end of the front-side separator and a front end of the rear-side separator are fitted to each other, thereby to connect the front-side connection portion of the front-side terminal member and the rear-side connection portion of the rear-side terminal member.

In the method for producing the gas sensor according to the present disclosure configured as described above, a jig is not needed, which is used for fixing either the front-side terminal member or the rear-side terminal member during the work for connecting the front-side connection portion and the rear-side connection portion. Thus, in the method for producing the gas sensor according to the present disclosure, when the front-side connection portion and the rear-side connection portion are connected to each other, the work for attaching/detaching the jig described above can be omitted, thereby improving production efficiency of gas sensors.

In the method for producing the gas sensor according to the present disclosure, the front-side terminal member and the rear-side terminal member are held by the front-side separator and the rear-side separator, respectively, after the front-side connection portion and the rear-side connection portion are connected to each other. Therefore, in the method for producing the gas sensor according to the present disclosure, it is possible to inhibit occurrence of a situation that connection between the front-side connection portion and the rear-side connection portion is canceled after the front-side connection portion and the rear-side connection portion are connected to each other, thereby improving stability of connection between the front-side connection portion and the rear-side connection portion.

In the still other aspect of the present disclosure, the separator may be formed such that an opening for exposing a connection portion between the front-side connection portion and the rear-side connection portion to the outside of the separator is provided in the vicinity of a portion in which the front-side separator and the rear-side separator come into contact with each other when the front-side separator and the rear-side separator are fitted to each other. In the still other aspect of the present disclosure, a welding step of welding the connection portion may be performed after the fitting step is ended.

In the method for producing the gas sensor according to the present disclosure configured as described above, since heat can be applied to the connection portion between the front-side connection portion and the rear-side connection portion from the outside of the separator via the opening, even if the separator holds the metal terminal in a state of surrounding the metal terminal, the connection portion between the front-side connection portion and the rear-side connection portion can be welded.

In the still other aspect of the present disclosure, specifically, the method for producing the gas sensor may include an opening determination step of detecting the position of the opening by photographing the opening from the outside of the separator before the connection portion is welded, and determining the position of the connection portion on the basis of a result of the detection, and in the welding step, welding may be performed at the position determined in the opening determination step. Alternatively, in the still other aspect of the present disclosure, specifically, the method for producing the gas sensor may include a boundary determination step of detecting a boundary between the front-side connection portion and the rear-side connection portion by photographing the opening from the outside of the separator before the connection portion is welded, and determining the position of the connection portion on the basis of a result of the detection, and in the welding step, welding may be performed at the position determined in the boundary determination step.

In the method for producing the gas sensor according to the present disclosure configured as described above, the front-side connection portion and the rear-side connection portion can be welded together with heat being accurately applied to the connection portion therebetween.

BRIEF DESCRIPTION OF THE DRAWINGS

These and other features and advantages of the present invention will become more readily appreciated when considered in connection with the following detailed description and appended drawings, wherein like designations denote like elements in the various views, and wherein:

FIGS. 16A and 16B are perspective views showing another embodiment of a front-side terminal member and a rear-side terminal member.

DETAILED DESCRIPTION OF THE INVENTION

An embodiment of the present disclosure will be described below with reference to the drawings.

A gas sensor 1 according to the present embodiment is an NOx sensor which detects NOx in an exhaust gas and is mounted to an exhaust pipe of an internal combustion engine such that a front end portion thereof projects into the exhaust pipe.

Figure 1:
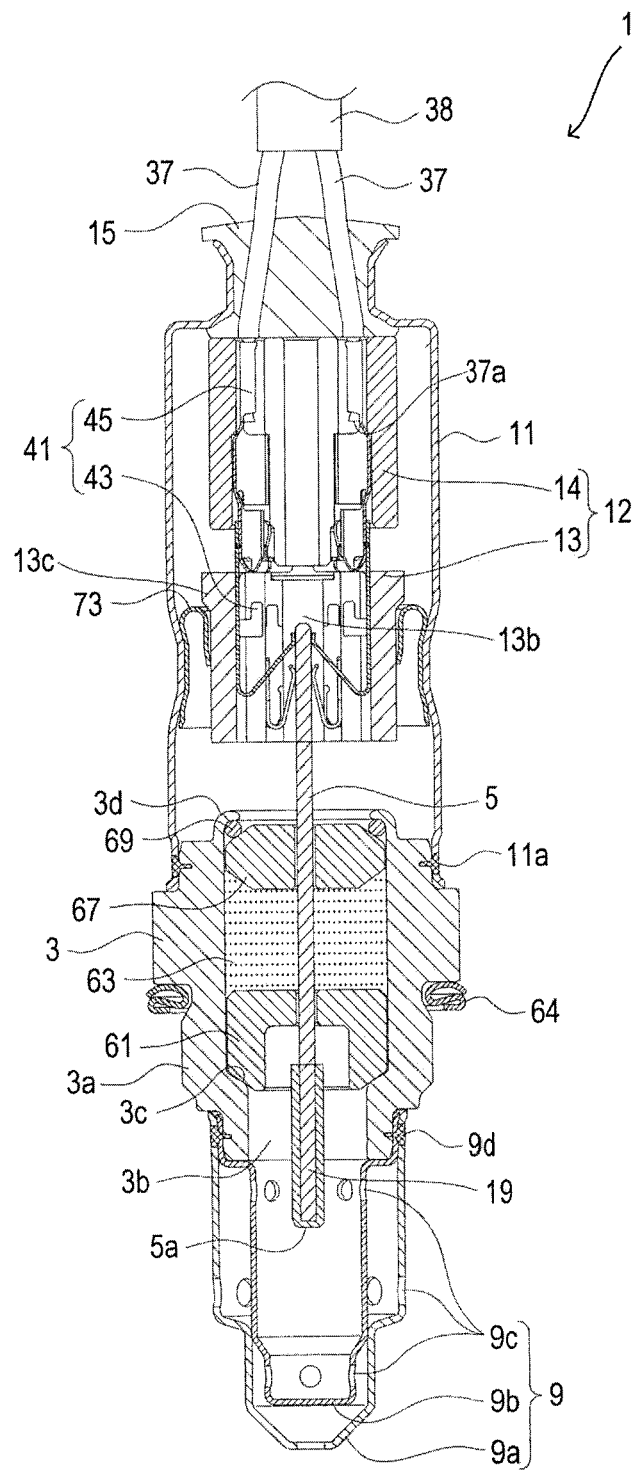
FIG. 1 is a cross-sectional view showing an entire structure of a gas sensor 1.

As shown in FIG. 1, the gas sensor 1 includes a metal shell 3, a detection element 5, an element protector 9, a sheath 11, an insulating separator 12, a closing member 15, a plurality of metal terminals 41, and a plurality of lead wires 37. In FIG. 1, the lower side of the gas sensor 1 is referred to as a front side, the upper side of the gas sensor 1 is referred to as a rear side, and the longitudinal direction of the gas sensor 1 is referred to as an axial direction.

The metal shell 3 is a tubular member formed from a heat-resistant metal such as stainless steel. The detection element 5 is formed in a long plate shape extending in the axial direction and is inserted into the metal shell 3. The element protector 9 is disposed at the front side of the metal shell 3 and covers a front end of the detection element 5. The sheath 11 is attached at the rear side of the metal shell 3 via a welding portion 11a and covers the outer periphery of the detection element 5. The insulating separator 12 is disposed inside the sheath 11, and houses a rear end of the detection element 5. The closing member 15 closes a rear end of the sheath 11.

Figure 2:
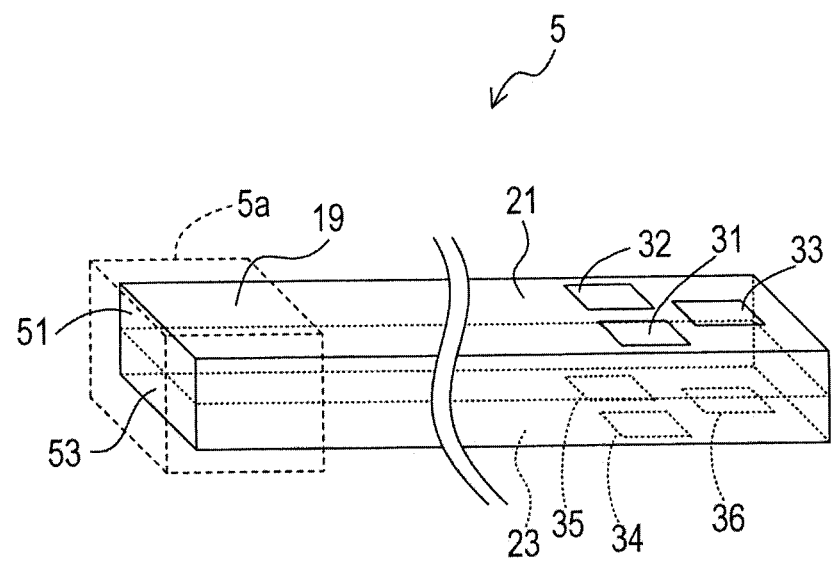
FIG. 2 is a perspective view showing a schematic structure of a detection element 5.

In the detection element 5, a detection portion 19 covered with a protection layer 5a is formed at the front side to be directed to an exhaust gas. As shown in FIG. 2, electrode terminal portions 31, 32, 33, 34, 35 and 36 are formed on a first plate surface 21 and a second plate surface 23, which are in a positional relation of front and back, of a rear-side outer surface of the detection element 5.

The detection element 5 is fixed inside the metal shell 3 such that the front-side detection portion 19 projects from the front end of the metal shell 3 which is to be fixed to the exhaust pipe, and the rear-side electrode terminal portions 31, 32, 33, 34, 35 and 36 project from the rear end of the metal shell 3, as shown in FIG. 1. The electrode terminal portions 31, 32, 33, 34, 35 and 36 are not shown in FIG. 1 but shown in FIG. 2.

A metal terminal 41 is connected to each of the electrode terminal portions 31, 32, 33, 34, 35 and 36. That is, a plurality of metal terminals 41 are disposed between the detection element 5 and the insulating separator 12 inside the insulating separator 12, and thereby are electrically connected to the respective electrode terminal portions 31, 32, 33, 34, 35 and 36 of the detection element 5. Each metal terminal 41 includes a front-side terminal member 43 and a rear-side terminal member 45.

The plurality of metal terminals 41 are electrically connected to a plurality of lead wires 37 arranged from the outside into the gas sensor 1, respectively. The structure of the metal terminal 41 will be described later in detail.

The metal terminals 41 and the lead wires 37 form a current path for a current that flows between the detection element 5 and external equipment (not shown) to which the lead wires 37 are connected. The plurality of lead wires 37 are bunched together by a tube member 38. In FIG. 1, only two lead wires 37 are shown.

As shown in FIG. 2, the detection element 5 has a rectangular parallelepiped shape obtained by stacking a plate-shaped element portion 51 extending in the axial direction onto a plate-shaped heater 53 also extending in the axial direction. The detection element 5 has a rectangular cross-section in a direction perpendicular to the axial direction. In FIG. 2, the protection layer 5a is shown by dotted lines. In FIG. 2, the detection element 5 is shown with an intermediate portion thereof in the axial direction being omitted.

Since the detection element 5 is a conventionally known detection element, the schematic structure thereof will be described below while omitting detailed description of the internal structure and the like thereof.

For example, the element portion 51 includes: an oxygen pump cell, a reference cell, and an NOx detection cell, each obtained by forming porous electrodes on opposed surfaces of a solid electrolyte substrate; and a spacer for forming a hollow oxygen measurement chamber and a hollow NOx measurement chamber. The solid electrolyte substrate is formed from, for example, zirconia in which yttria is dissolved as a stabilizer. The porous electrodes are formed from, for example, Pt as a principal component. The spacer forming the oxygen measurement chamber and the NOx measurement chamber is formed from alumina as a principal component. Inside the hollow oxygen measurement chamber, one of the opposed porous electrodes of each of the oxygen pump cell and the reference cell is exposed. The spacer is formed such that the oxygen measurement chamber is located on at least the front side of the element portion 51. The spacer is provided with a gas passage for introducing a gas to be measured from the outside into the oxygen measurement chamber via a diffusion control portion. Inside the NOx measurement chamber, one of the opposed porous electrodes of the NOx detection element is exposed. A portion, of the element portion 51, in which the porous electrodes, the oxygen measurement chamber, and the NOx measurement chamber are formed corresponds to the detection portion 19.

On the other hand, the heater 53 is formed by sandwiching a heat-generating resistor pattern containing Pt as a principal component between insulating substrates containing alumina as a principal component. The element portion 51 and the heater 53 are joined to each other via a ceramic layer.

In the detection element 5 as described above, as shown in FIG. 2, three electrode terminal portions 31, 32 and 33 are formed at the rear side (i.e., right side in FIG. 2) of the first plate surface 21, while the three electrode terminal portions 34, 35 and 36 are formed at the rear side of the second plate surface 23. The electrode terminal portions 31, 32 and 33 are formed on the element portion 51, and are electrically connected to the pair of porous electrodes of the oxygen pump cell and to one of the porous electrodes of the reference cell, respectively. The electrode terminal portions 34, 35 and 36 are formed on the heater 53, and are connected to the opposed ends of the heat-generating resistor pattern and to one of the porous electrodes of the NOx detection element, respectively, via a via conductor (not shown) that crosses the heater in the thickness direction of the heater.

As shown in FIG. 1, the metal shell 3 is a tubular member having, on an outer surface thereof, a screw portion 3a for fixing the metal shell 3 to the exhaust pipe, and having a through-hole 3b at the axial center thereof. In the through-hole 3b, a ledge portion 3c projecting radially inward is formed. The metal shell 3 is formed from a metal material (e.g., stainless steel).

Inside the through-hole 3b of the metal shell 3, an annular ceramic holder 61 which is disposed so as to surround the periphery of the detection element 5 in the radial direction and is formed using an insulating material (e.g., alumina), a talc ring 63 having a similar annular shape, and a ceramic sleeve 67 which has a similar annular shape and is formed using an insulating material (e.g., alumina), are stacked in order from the front side to the rear side.

A crimping packing 69 is disposed between the ceramic sleeve 67 and a rear end portion 3d of the metal shell 3. The rear end portion 3d of the metal shell 3 is crimped through the crimping packing 69 so as to press the ceramic sleeve 67 toward the front side.

An annular gasket 64 is disposed at a portion, of the outer periphery of the metal shell 3, on the rear side of the screw portion 3a. The gasket 64 is a member for inhibiting leakage of gas from a gap between the gas sensor 1 and a sensor attachment position.

The element protector 9 is a tubular member attached through a welding portion 9d to the front-side outer periphery of the metal shell 3 so as to cover the projecting portion of the detection element 5. The element protector 9 is formed using a heat-resistant material (e.g., SUS310S). The element protector 9 has a double structure including an external protector 9a and an internal protector 9b. Each of the external protector 9a and the internal protector 9b has, at a side wall or a front end thereof, a plurality of holes 9c which allow gas to pass therethrough.

The insulating separator 12 is configured to be separable into a front-side separator 13 and a rear-side separator 14.

The front-side separator 13 is a tubular member formed using an insulating material (e.g., alumina), and is held in the sheath 11 by a tubular metal holder 73 disposed in the sheath 11. Inside the front-side separator 13, a terminal arrangement hole 13b penetrating in the axial direction is formed. The terminal arrangement hole 13b houses therein the rear end portion (i.e., the electrode terminal portions 31, 32, 33, 34, 35 and 36) of the detection element 5, and front end portions of the plurality of metal terminals 41 (i.e., the front-side terminal members 43) electrically connected to the electrode terminal portions 31, 32, 33, 34, 35 and 36. The front-side separator 13 has, on an outer surface thereof, an annular flange portion 13c protruding outward. The installation position, of the front-side separator 13, in the axial direction inside the sheath 11 is determined by the flange portion 13c coming into contact with the metal holder 73.

The rear-side separator 14 is a tubular member formed using an insulating material (e.g., alumina), and is disposed in the sheath 11, at the front side of the closing member 15. Inside the rear-side separator 14, a plurality of terminal arrangement holes penetrating in the axial direction are formed. In the rear-side separator 14, rear end portions of the metal terminals 41 (i.e., the rear-side terminal members 45) are housed in the plurality of terminal arrangement holes, respectively.

The closing member 15 is a grommet formed using a flexible material (e.g., fluororesin). The closing member 15 is disposed in a rear-side opening of the sheath 11, and is fixed in the sheath 11 by the sheath 11 being crimped inward from the outside. The closing member 15 has a plurality of through-holes (not shown) through which the plurality of lead wires 37 are inserted.

The plurality lead wires 37 are respectively connected by crimping to the rear ends of different metal terminals 41, and are inserted in the through-holes penetrating the closing member 15 to be extended to the outside.

Next, the metal terminal 41 will be described.

As described above, each metal terminal 41 includes the front-side terminal member 43 and the rear-side terminal member 45.

Figure 3:
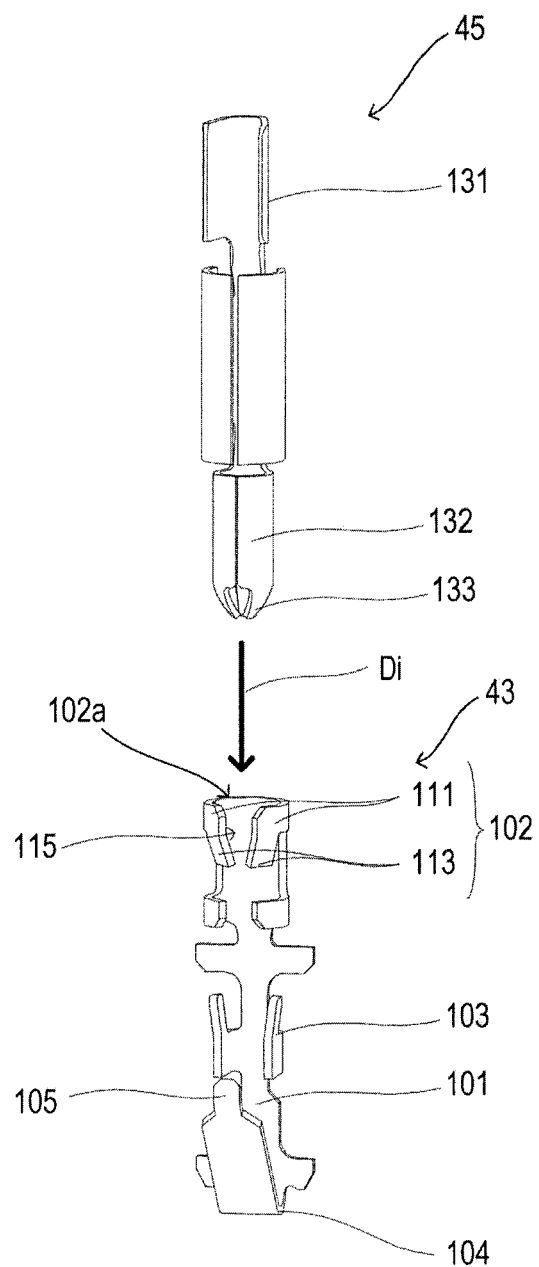
FIG. 3 is a perspective view showing a front-side terminal member 43 and a rear-side terminal member 45.

The front-side terminal member 43 is formed from a metal material capable of maintaining elasticity even after being repeatedly exposed to high temperature. For example, the front-side terminal member 43 is formed using an alloy material (e.g., NCF718) containing nickel as a principal component. As shown in FIG. 3, the front-side terminal member 43 is formed by bending a long and thin plate-shaped metal material, and includes a main body 101, a female connection portion 102, extension portions 103, a bent portion 104, and an element contact portion 105.

The main body 101 is formed in a long plate shape extending in the axial direction.

The female connection portion 102 has two housing portions 111 and two terminal contact portions 113.

Each of the two housing portions 111 is provided at the rear side of the main body 101 so as to extend from the opposed end portions of the main body 101 along a transverse direction (i.e., a direction perpendicular to the axial direction) of the main body 101. The two housing portions 111 and the main body 101 form a shape capable of surrounding a male connection portion 132 described later. Thus, at the rear-side end portion of the female connection portion 102, an insertion port 102a for inserting the rear-side terminal member 45 is formed. In FIG. 3, an arrow Di indicates an insertion direction in which the rear-side terminal member 45 is inserted in the insertion port 102a of the female connection portion 102.

The female connection portion 102 has a cutout portion 115 at a position opposed to the main body 101. Thereby, a portion for surrounding the male connection portion 132 by the two housing portions 111 and the main body 101 is formed such that a cross-sectional shape thereof perpendicular to the axial direction is a circle having a cutout at a certain position.

The two terminal contact portions 113 are provided so as to correspond to the two housing portions 111, respectively. Each terminal contact portion 113 is provided extending from the corresponding housing portion 111 toward the front side in the axial direction, near the cutout portion 115 of the housing portion 111, and is bent inward at a portion connected to the housing portion 111 so that the diameter thereof is decreased toward the front side.

The extension portions 103 are provided extending from the opposed end portions of the main body 101 along the transverse direction of the main body 101, and the direction in which the extension portions 103 extend is a direction substantially perpendicular to the plate surface of the main body 101. Having the extension portions 103, the strength of the front-side terminal member 43 is increased.

At the front side of the main body 101, the bent portion 104 is formed by bending the main body 101 in the direction perpendicular to the plate surface of the main body 101. The bent portion 104 is a connection portion connecting the main body 101 and the element contact portion 105.

The element contact portion 105 is connected to the main body 101 via the bent portion 104, and is formed such that the dimension of a gap between the element contact portion 105 and the main body 101 is variable according to elastic deformation of the bent portion 104.

In the front-side terminal member 43 formed as described above, when the element contact portion 105 comes into contact with any of the electrode terminal portions 31, 32, 33, 34, 35 and 36 of the detection element 5, the contact state between the element contact portion 105 and the detection element 5 can be maintained by elastic deformation of the bent portion 104.

The rear-side terminal member 45 is formed using, for example, a stainless steel alloy (e.g., SUS304). The rear-side terminal member 45 is formed by bending a long and thin plate-shaped metal material, and includes a signal line connection portion 131 and a male connection portion 132.

The signal line connection portion 131 is deformed by bending to be formed in a tubular shape capable of surrounding a core 37a of the lead wire 37. The core 37a of the lead wire 37 is not shown in FIG. 3 but shown in FIG. 1. The signal line connection portion 131 is connected to the core 37a of the lead wire 37 by being crimped radially inward while surrounding the core 37a of the lead wire 37.

At the front side of the signal line connection portion 131, the male connection portion 132 is formed in a tubular shape so as to have a circular cross-section in a direction perpendicular to the axial direction. The outer diameter of the male connection portion 132 is set to be smaller than the inner diameter of the insertion port 102a of the female connection portion 102. The male connection portion 132 has a diameter reduction portion 133 at the front side. The diameter reduction portion 133 is formed in a shape the diameter of which decreases toward the front side.

The rear-side terminal member 45 formed as described above is electrically connected to external equipment via the lead wire 37 when the signal line connection portion 131 is electrically connected to the core 37a of the lead wire 37.

Figure 4:
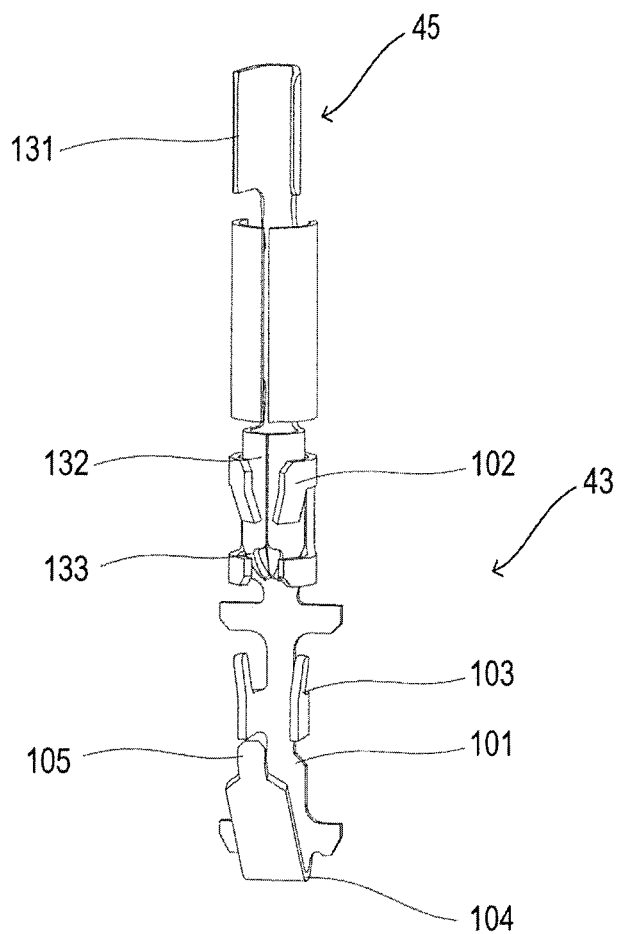
FIG. 4 is a perspective view showing the front-side terminal member 43 and the rear-side terminal member 45 being connected to each other, as viewed from the front.
Figure 5:
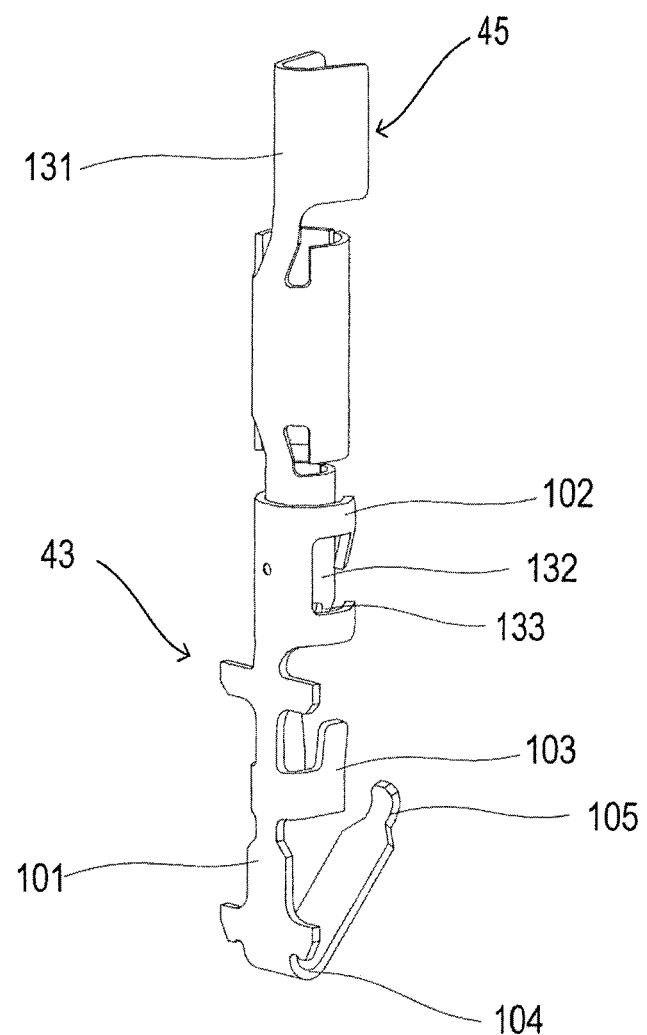
FIG. 5 is a perspective view showing the front-side terminal member 43 and the rear-side terminal member 45 being connected to each other, as viewed from the back.

As shown in FIGS. 4 and 5, the front-side terminal member 43 and the rear-side terminal member 45 are connected to each other when the male connection portion 132 is inserted into the female connection portion 102.

Figure 6:
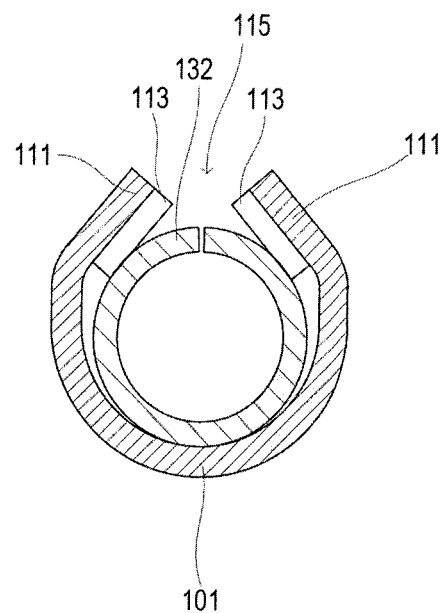
FIG. 6 is a cross-sectional view showing the front-side terminal member 43 and the rear-side terminal member 45 being connected to each other, taken along a direction perpendicular to an axial direction.
Figure 7:
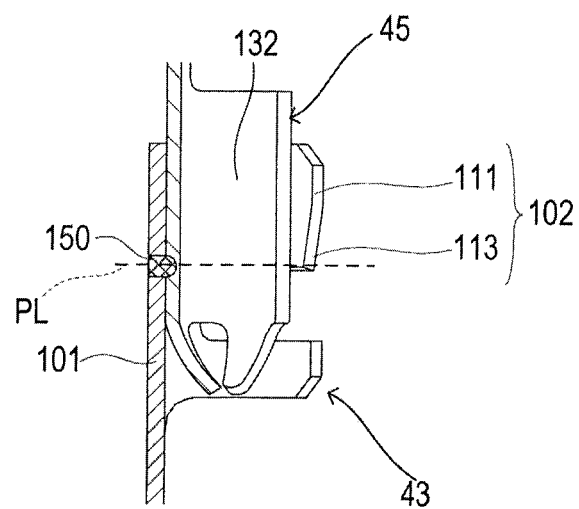
FIG. 7 is a cross-sectional view showing the front-side terminal member 43 and the rear-side terminal member 45 being connected to each other, taken along the axial direction.

When the male connection portion 132 is inserted into the female connection portion 102, as shown in FIGS. 6 and 7, front-side ends of the terminal contact portions 113 of the female connection portion 102 come into contact with the outer peripheral surface of the male connection portion 132, and press the male connection portion 132 inward. As described above, the terminal contact portions 113 are disposed near the cutout portion 115 which is opposed to the main body 101. Therefore, when the terminal contact portions 113 press the male connection portion 132 inward, the female connection portion 102 and the male connection portion 132 are connected to each other with the outer peripheral surface of the male connection portion 132 being in contact with the inner peripheral surface of the main body 101. Then, as shown in FIG. 7, a portion of an area where the male connection portion 132 and the main body 101 are in contact with each other is welded to form a welding portion 150, whereby the rear-side terminal member 45 is attached to the front-side terminal member 43. In the present embodiment, the position of the welding portion 150 is set such that the welding portion 150 and the front-side end of each terminal contact portion 113 (i.e., a contact point between the terminal contact portion 113 and the male connection portion 132) are located on the same plane PL perpendicular to the axial direction.

Figure 16A:
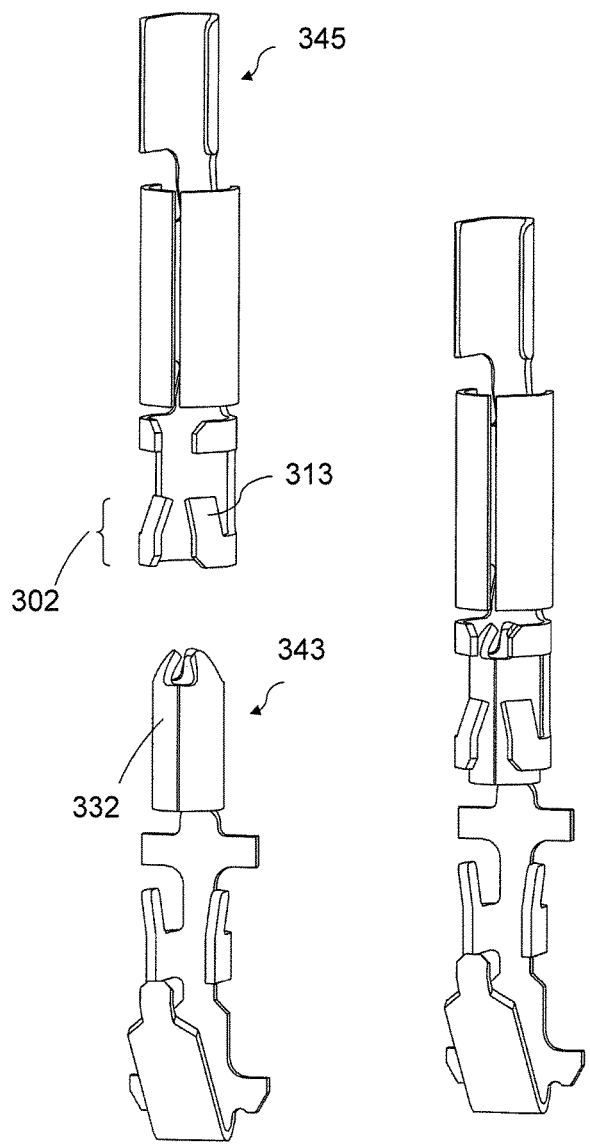
Figures 17A, 17B:
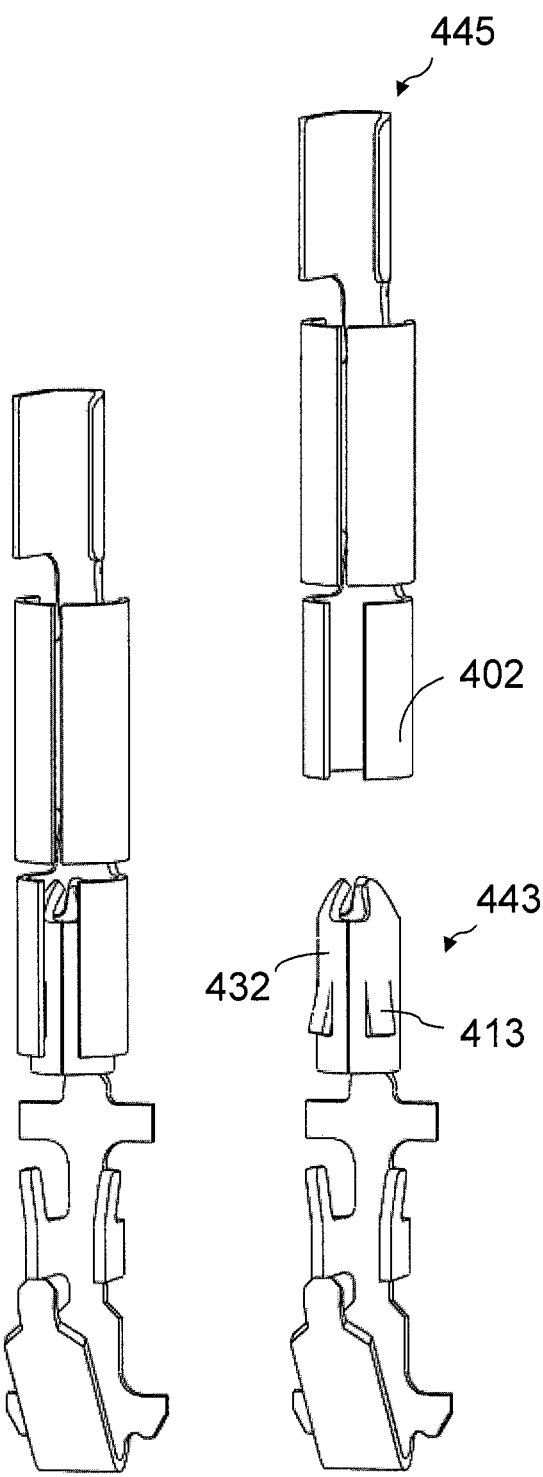
FIGS. 17A and 17B are perspective views showing an additional embodiment of a front-side terminal member and a rear-side terminal member.
Figures 18A, 18B:
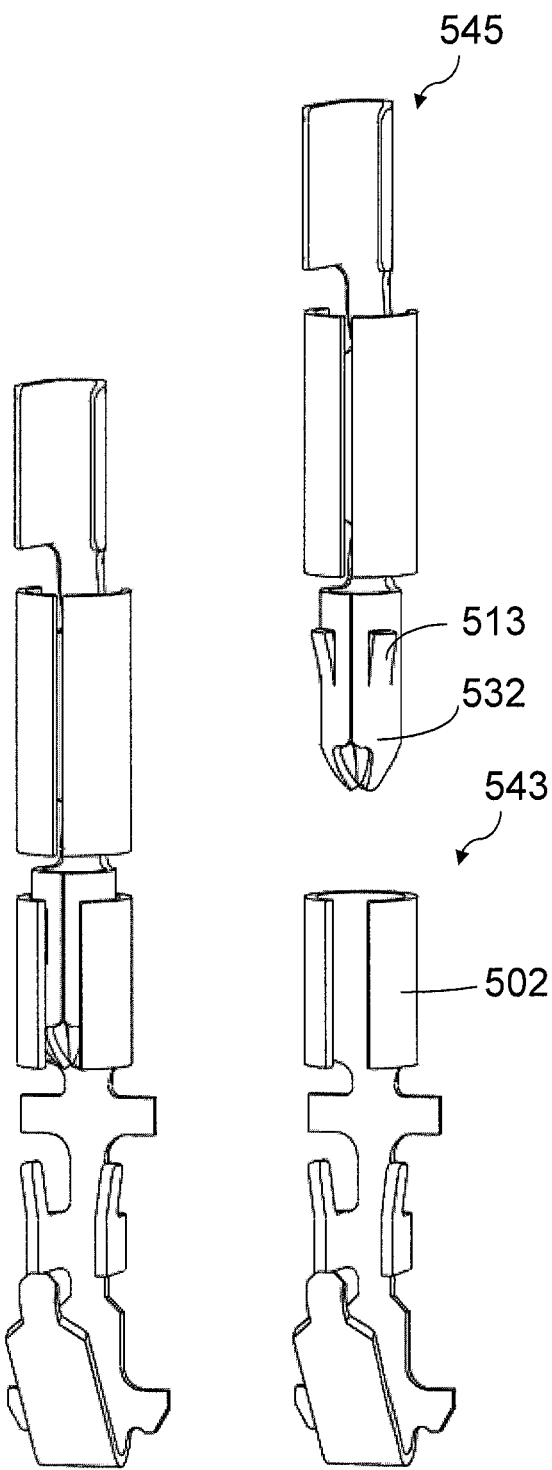
FIGS. 18A and 18B are perspective views showing a still further additional embodiment of a front-side terminal member and a rear-side terminal member.

In one embodiment, as shown in FIGS. 16A and 16B, the front-side connection portion 343 includes a male connection portion 332 and the rear-side connection portion 345 includes a female connection portion 302, which contains a terminal connection portion 313. In another embodiment, as shown in FIGS. 17A and 17B, the front-side connection portion 443 includes a male connection portion 432 and the rear-side connection portion 445 includes a female connection portion 402. The male connection portion 432 contains a terminal connection portion 413. Further in another embodiment, as shown in FIGS. 18A and 18B, the front-side connection portion 543 includes a female connection portion 502 and the rear-side connection portion 545 includes a male connection portion 532, which contains a terminal connection portion 513.

Next, a step of connecting the front-side terminal member 43 and the rear-side terminal member 45, in a process of manufacturing the gas sensor 1, will be described.

Figure 8:
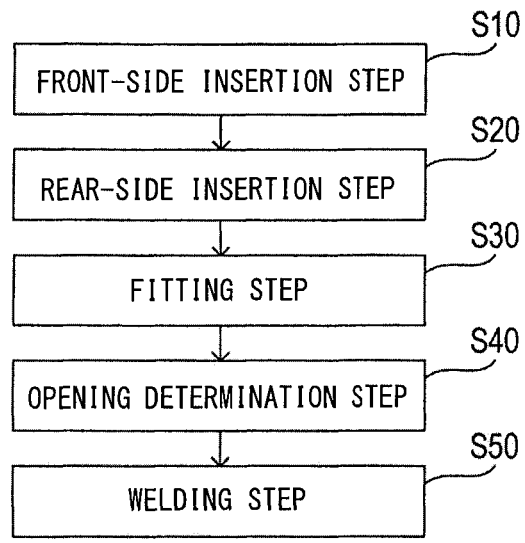
FIG. 8 is a flowchart showing process steps for connecting the front-side terminal member 43 and the rear-side terminal member 45.
Figures 9A, 9B:
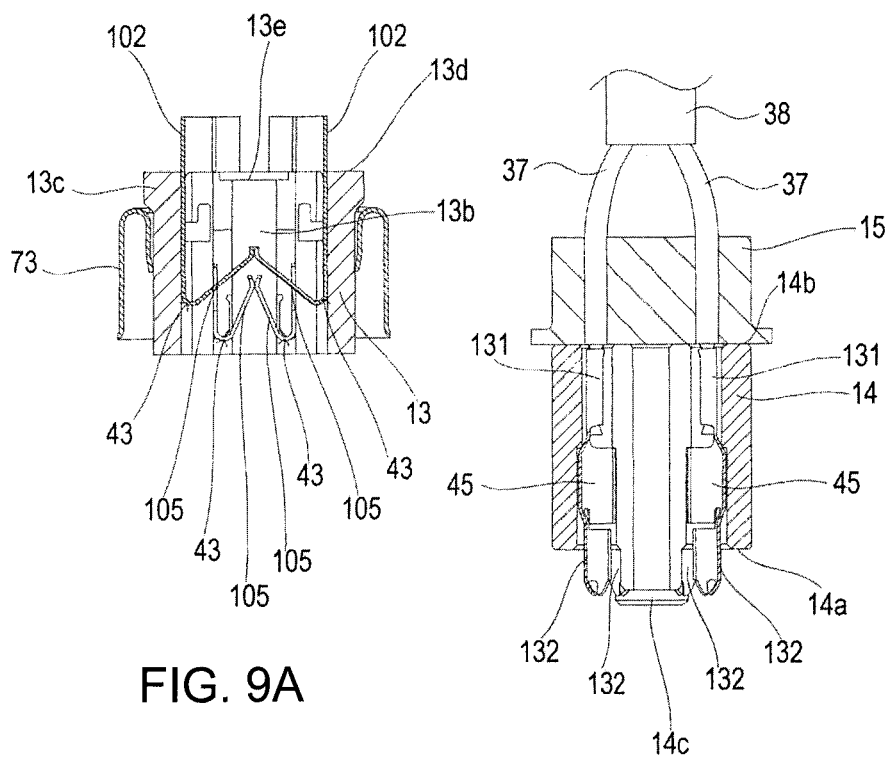
FIGS. 9A and 9B are cross-sectional views showing a front-side separator 13 (FIG. 9A) and a rear-side separator 14 (FIG. 9B).

As shown in FIG. 8, first, a front-side insertion step is performed at S10. In the front-side insertion step, as shown in FIG. 9A, the four front-side terminal members 43 are inserted into four openings formed at a rear-side surface 13d of the front-side separator 13, respectively. Thereby, the front-side terminal members 43 are held in the front-side separator 13 such that the female connection portions 102 of the front-side terminal members 43 project from the rear-side surface 13d of the front-side separator 13 and the element contact portions 105 thereof are housed in the terminal arrangement hole 13b. At the rear-side surface 13d of the front-side separator 13, a recess 13e for fitting the front-side separator 13 to the rear-side separator 14 is formed.

When the front-side insertion step at S10 is ended, as shown in FIG. 8, a rear-side insertion step is performed at S20. In the rear-side insertion step, as shown in FIG. 9B, first, six lead wires 37 are inserted into six openings which are formed at a rear-side surface 14b of the rear-side separator 14, respectively. Then, the lead wires 37 are drawn out from six openings formed at a front-side surface 14a of the rear-side separator 14, and are connected to the signal line connection portions 131 of the rear-side terminal members 45 at the front side of the rear-side separator 14. Then, four lead wire 37 are drawn out from four openings formed at the rear-side surface 14b of the rear-side separator 14. Thereby, the rear-side terminal members 45 are held in the rear-side separator 14 such that the male connection portions 132 thereof project from the front-side surface 14a of the rear-side separator 14. At the front-side surface 14a of the rear-side separator 14, a projection 14c for fitting the rear-side separator 14 to the front-side separator 13 is formed. As shown in FIG. 9B, the lead wires 37 are bunched together by the tube member 38 before being inserted into the rear-side separator 14.

Figure 10:
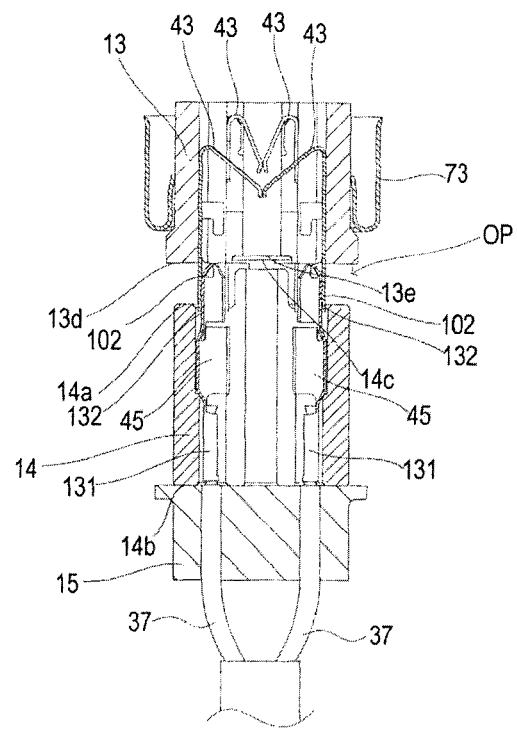
FIG. 10 is a cross-sectional view showing the front-side separator 13 and the rear-side separator 14 being connected.

When the rear-side insertion step at S20 is ended, a fitting step is performed at S30 as shown in FIG. 8. In the fitting step, as shown in FIG. 10, the projection 14c of the rear-side separator 14 is fitted in the recess 13e of the front-side separator 13. Thereby, the front-side separator 13 and the rear-side separator 14 are connected to each other with the female connection portions 102 of the front-side terminal members 43 being connected to the male connection portions 132 of the rear-side terminal members 45. The front-side separator 13 and the rear-side separator 14 being connected to each other cause an opening OP to be formed therebetween.

Figure 11:
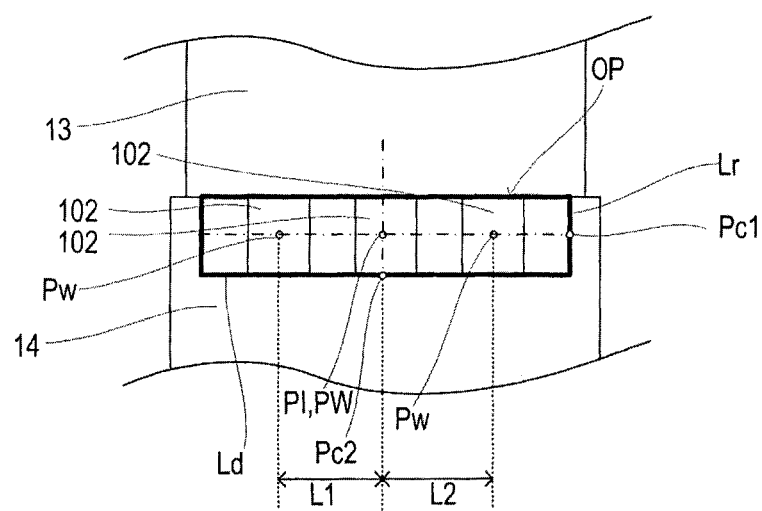
FIG. 11 is a diagram showing an opening OP and its periphery.

When the fitting step at S30 is ended, an opening determination step is performed at S40 as shown in FIG. 8. In the opening determination step, the opening OP is photographed by a camera (not shown) from the outside of the front-side separator 13 and the rear-side separator 14. As shown in FIG. 11, the female connection portions 102 are exposed via the opening OP formed between the front-side separator 13 and the rear-side separator 14.

Image data obtained by the camera photographing is inputted to a control unit of a laser welding apparatus (not shown). The control unit is configured to execute various control processes in the laser welding apparatus, and is predominantly composed of a known microcomputer including a CPU, a ROM, a RAM, an input port, an output port, bus lines connecting these components, etc.

The control unit extracts the opening OP from the inputted image data through a known image recognition process. Then, the control unit detects the position of the opening OP in an area photographed by the camera, on the basis of the extracted opening OP. Then, the control unit determines welding points Pw exposed via the opening OP, on the basis of the detected position of the opening OP. For example, as shown in FIG. 11, among four sides forming the rectangular shape of the opening OP, a midpoint Pc1 of a right side Lr and a midpoint Pc2 of a lower side Ld are obtained. Next, an intersection point Pi of an imaginary line that passes the midpoint Pc1 and is parallel to the lower side Ld and an imaginary line that passes the midpoint Pc2 and is parallel to the right side Lr is obtained. The intersection point Pi, a position apart leftward from the intersection point Pi by a predetermined distance L1, and a position apart rightward from the intersection point Pi by a predetermined distance L2, are determined as the positions of the welding points Pw.

When the opening determination step at S40 is ended, a welding step is performed at S50 as shown in FIG. 8. In the welding step, the control unit of the laser welding apparatus sets a laser irradiation portion for a laser irradiation unit such that laser beam is applied to the positions determined at S40, and thereafter causes the laser irradiation unit to emit laser beam. Thereby, the rear-side terminal member 45 is attached to the front-side terminal member 43 by welding at the welding points Pw.

Upon ending the welding step at S50, the process of connecting the front-side terminal member 43 and the rear-side terminal member 45 is ended.

The metal terminal 41 formed as described above is used in the gas sensor 1 which includes: the detection element 5 having the electrode terminal portions 33 and 36; and the lead wire 37. The electrode terminal portions 33 and 36 output, to the outside, a detection signal indicating the result of detection of NOx in the exhaust gas. The lead wire 37 form a signal path for outputting the detection signal to the outside. The metal terminal 41 is electrically connected to the electrode terminal portions 33 and 36 and the lead wire 37 in order to transfer the detection signal from the electrode terminal portions 33 and 36 to the lead wire 37.

The metal terminal 41 includes: the front-side terminal member 43 which comes into contact with the electrode terminal portions 33 and 36; and the rear-side terminal member 45 which is connected to the lead wire 37. The front-side terminal member 43 includes the female connection portion 102 for connection with the rear-side terminal member 45. The rear-side terminal member 45 includes the male connection portion 132 for connection with the front-side terminal member 43.

Further, the female connection portion 102 has the insertion port 102a through which the male connection portion 132 is inserted into the female connection portion 102. The outer diameter of the male connection portion 132 is set to be smaller than the inner diameter of the insertion port 102a of the female connection portion 102. Thus, the insertion port 102a is formed in a shape that can prevent the insertion port 102a and the male connection portion 132 from coming into contact with each other when the male connection portion 132 is inserted into the female connection portion 102 through the insertion port 102a. The insertion port 102a and the male connection portion 132 being prevented from coming into contact with each other means that, when the male connection portion 132 is inserted in the insertion port 102a of the female connection portion 102, at least portions thereof are separated from each other. The outer diameter of the male connection portion 132 may be set to be smaller than the inner diameter of the insertion port 102a of the female connection portion 102 as in the present embodiment. Alternatively, it is sufficient that the cross-sectional area of the male connection portion 132 is smaller than the cross-sectional area of the insertion port 102a of the female connection portion 102.

The female connection portion 102 includes the terminal contact portions 113 which bring the male connection portion 132 and the female connection portion 102 into contact with each other by pressing the male connection portion 132 toward the female connection portion 102 inside the female connection portion 102, when the male connection portion 132 is inserted into the female connection portion 102.

As described above, in the metal terminal 41, the insertion port 102a of the female connection portion 102 is formed in a shape that prevents the insertion port 102a and the male connection portion 132 from coming into contact with each other when the male connection portion 132 is inserted therein. Therefore, the metal terminal 41 can inhibit occurrence of a situation that, when the male connection portion 132 is inserted into the female connection portion 102, the insertion work is interfered by contact of the female connection portion 102 and the male connection portion 132. Thus, efficiency of the work for connecting the female connection portion 102 and the male connection portion 132 can be improved.

Further, in the metal terminal 41, the terminal contact portions 113 bring the male connection portion 132 and the female connection portion 102 into contact with each other by pressing the male connection portion 132 toward the female connection portion 102 inside the female connection portion 102. Thus, the metal terminal 41 can hold the state where the male connection portion 132 and the female connection portion 102 are in contact with each other after the male connection portion 132 is inserted into the female connection portion 102. Therefore, welding can be performed at the positions where the male connection portion 132 and the female connection portion 102 are in contact with each other. Thus, the metal terminal 41 can inhibit occurrence of a situation that a gap is formed at the welding portion 150 at which the female connection portion 102 and the male connection portion 132 are fixed to each other by welding, thereby improving stability of welding.

Two terminal contact portions 113 are provided in the direction perpendicular to the insertion direction Di along which the male connection portion 132 is inserted into the female connection portion 102. Thus, the metal terminal 41 can restrict movement of the male connection portion 132 along the direction perpendicular to the insertion direction Di inside the female connection portion 102, thereby improving stability of the position of the male connection portion 132 inside the female connection portion 102.

The female connection portion 102 has the terminal contact portions 113. In the metal terminal 41, a material capable of maintaining elasticity even after being repeatedly exposed to high temperature is used as a material of the front-side terminal member 43 in order to maintain the contact with the electrode terminal portions 33 and 36 by the front-side terminal member 43. Therefore, in the metal terminal 41, since the female connection portion 102 has the terminal contact portions 113, the terminal contact portions 113 can also be formed from the material capable of maintaining elasticity even after being repeatedly exposed to high temperature. Therefore, the metal terminal 41 can inhibit deterioration in the function of bringing the male connection portion 132 and the female connection portion 102 into contact with each other by pressing the male connection portion 132.

The contact point at which each terminal contact portion 113 contacts the male connection portion 132 and the welding portion 150 at which the female connection portion 102 and the male connection portion 132 are welded together, are located on the same plane PL perpendicular to the insertion direction Di. Thus, the terminal contact portions 113 press the male connection portion 132 toward the female connection portion 102 near the welding portion 150, and therefore, contact of the female connection portion 102 and the male connection portion 132 at the welding portion 150 can be made stronger, thereby further improving stability of welding.

The method for producing the gas sensor 1 includes the front-side insertion step, the rear-side insertion step, and the fitting step. The insulating separator 12 holds the metal terminals 41 in a state of surrounding the metal terminals 41. The insulating separator 12 includes: the front-side separator 13 which holds the front-side terminal members 43 in a state of surrounding the front-side terminal members 43; and the rear-side separator 14 which holds the rear-side terminal members 45 in a state of surrounding the rear-side terminal members 45.

In the front-side insertion step, the front-side terminal members 43 are inserted into the front-side separator 13, with the female connection portions 102 of the front-side terminal members 43 being positioned at the rear side of the front-side separator 13.

In the rear-side insertion step, the rear-side terminal members 45 are inserted into the rear-side separator 14, with the male connection portions 132 of the rear-side terminal members 45 being positioned at the front side of the rear-side separator 14.

In the fitting step, the rear end of the front-side separator 13 and the front end of the rear-side separator 14 are fitted to each other, thereby connecting the female connection portions 102 of the front-side terminal members 43 and the male connection portions 132 of the rear-side terminal members 45.

As described above, in the method for producing the gas sensor 1, a jig is not needed, which is used for fixing either the front-side terminal member 43 or the rear-side terminal member 45 during the work for connecting the female connection portion 102 and the male connection portion 132. Thus, in the method for producing the gas sensor 1, when the female connection portion 102 and the male connection portion 132 are connected to each other, the work for attaching/detaching the jig described above can be omitted, thereby improving production efficiency of the gas sensor 1.

In the method for producing the gas sensor 1, the front-side terminal members 43 and the rear-side terminal members 45 are held by the front-side separator 13 and the rear-side separator 14, respectively, after the female connection portions 102 and the male connection portions 132 are connected to each other. Therefore, in the method for producing the gas sensor 1, it is possible to inhibit occurrence of a situation that connection between the female connection portions 102 and the male connection portions 132 is canceled after the female connection portions 102 and the male connection portions 132 are connected to each other, thereby improving stability of connection between the female connection portions 102 and the male connection portions 132.

The insulating separator 12 is formed such that the opening OP for exposing the connection portion between the female connection portion 102 and the male connection portion 132 to the outside of the insulating separator 12 is provided in the vicinity of the portion in which the front-side separator 13 comes into contact with the rear-side separator 14 when the front-side separator 13 and the rear-side separator 14 are fitted to each other. The method for producing the gas sensor 1 includes the welding step of welding the connection portion between the female connection portion 102 and the male connection portion 132 after the fitting step is ended.

As described above, in the method for producing the gas sensor 1, since heat can be applied to the connection portions between the female connection portions 102 and the male connection portions 132 from the outside of the insulating separator 12 via the opening OP, even if the insulating separator 12 holds the metal terminals 41 in a state of surrounding the metal terminals 41, the connection portions between the female connection portions 102 and the male connection portions 132 can be welded.

Specifically, the method for producing the gas sensor 1 includes the opening determination step of: before welding the connection portion, photographing the opening OP from the outside of the insulating separator 12 to detect the position of the opening OP; and determining the position of the connection portion on the basis of the result of the detection. Then, in the method for producing the gas sensor 1, in the welding step, welding is performed at the position determined in the opening determination step. Thus, in the method for producing the gas sensor 1, the female connection portion 102 and the male connection portion 132 can be welded together with heat being accurately applied to the connection portion therebetween.

The metal terminal 41 corresponds to a metal terminal for a gas sensor, oxygen in the exhaust gas corresponds to a detection target gas, the electrode terminal portion 33, 36 corresponds to an electrode terminal portion, the detection element 5 corresponds to a sensor element, and the lead wire 37 corresponds to a signal line.

The female connection portion 102 corresponds to a front-side connection portion, the male connection portion 132 corresponds to a rear-side connection portion, the welding portion 150 corresponds to a welding point, and the plane PL corresponds to a plane.

In addition, the insulating separator 12 corresponds to a separator.

While one embodiment of the present disclosure has been described above, the present disclosure is not limited to the above embodiment, and can be carried out in various modes.

For example, in the aforementioned embodiment, the front-side terminal member 43 includes the female connection portion 102, and the rear-side terminal member 45 includes the male connection portion 132. However, the front-side terminal member 43 may include the male connection portion, and the rear-side terminal member 45 may include the female connection portion.

In the aforementioned embodiment, the female connection portion 102 includes the terminal contact portion 113. However, the male connection portion 132 may include the terminal contact portion.

Figure 12:
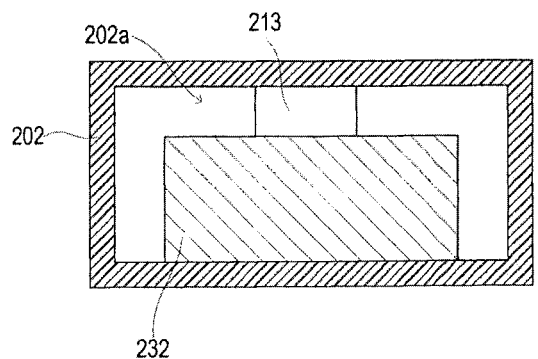
FIG. 12 is a cross-sectional view showing a front-side terminal member and a rear-side terminal member being connected to each other, taken along the direction perpendicular to the axial direction, according to another embodiment.

In the aforementioned embodiment, the insertion port 102a of the female connection portion 102 has a circular shape. However, the shape of the insertion port is not limited to the circular shape, and may be any shape as long as the insertion port can accommodate the male connection portion. For example, the insertion port of the female connection portion may have a rectangular shape as shown in FIG. 12, or may have a triangular shape or a polygonal shape with five or more sides. FIG. 12 shows a state in which a male connection portion 232 having a rectangular cross-section is inserted into a female connection portion 202 having a rectangular insertion port 202a, and the male connection portion 232 is pressed by a terminal contact portion 213 included in the female connection portion 202.

Figure 13:
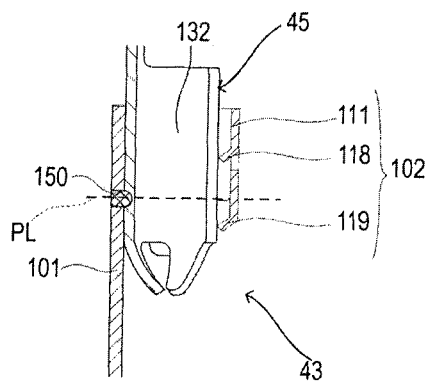
FIG. 13 is a cross-sectional view showing the front-side terminal member and the rear-side terminal member being connected to each other, taken along the axial direction, according to the other embodiment.

In the aforementioned embodiment, two terminal contact portions 113 are provided along the direction perpendicular to the insertion direction Di. However, as shown in FIG. 13, at least two terminal contact portions may be provided along the insertion direction Di. FIG. 13 shows a state in which a male connection portion 132 is inserted into a female connection portion 102 including terminal contact portions 118 and 119 disposed along the insertion direction Di, instead of the terminal contact portions 113. Thus, movement of the male connection portion 132 along the insertion direction Di can be restricted inside the female connection portion 102, thereby improving stability of the position of the male connection portion 132 inside the female connection portion 102.

In the aforementioned embodiment, the welding portion 150 and the contact point at which each terminal contact portion 113 contacts the male connection portion 132, are located on the same plane PL perpendicular to the insertion direction Di. However, as shown in FIG. 13, a first contact point at which the terminal contact portion 118 contacts the male connection portion 132 and a second contact point at which the terminal contact portion 119 contacts the male connection portion 132 may be located at positions opposite to each other with the plane PL therebetween. In this case, the state where the female connection portion 102 and the male connection portion 132 are in contact with each other is maintained by the terminal contact portions 118 and 119 located on the opposite sides with the plane PL therebetween, whereby contact of the female connection portion 102 and the male connection portion 132 at the welding portion 150 can be made stronger, resulting in further improved stability of welding. The terminal contact portion 118 corresponds to a first terminal contact portion, the terminal contact portion 119 corresponds to a second terminal contact portion, and the plane PL corresponds to a welding plane.

Figure 14:
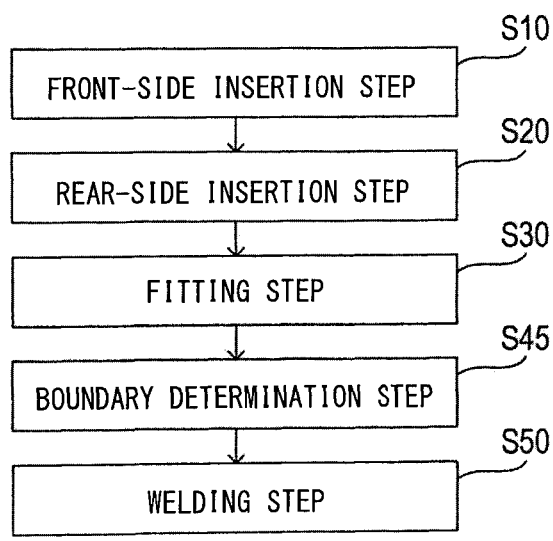
FIG. 14 is a flowchart showing process steps for connecting the front-side terminal member 43 and the rear-side terminal member 45 according to the other embodiment.

In the aforementioned embodiment, the opening determination step is performed at S40. However, as shown in FIG. 14, instead of the opening determination step at S40, a boundary determination step may be performed. That is, when the fitting step at S30 is ended, the boundary determination step is performed at S45. When the boundary determination step at S45 is ended, the welding step is performed at S50.

Figure 15:
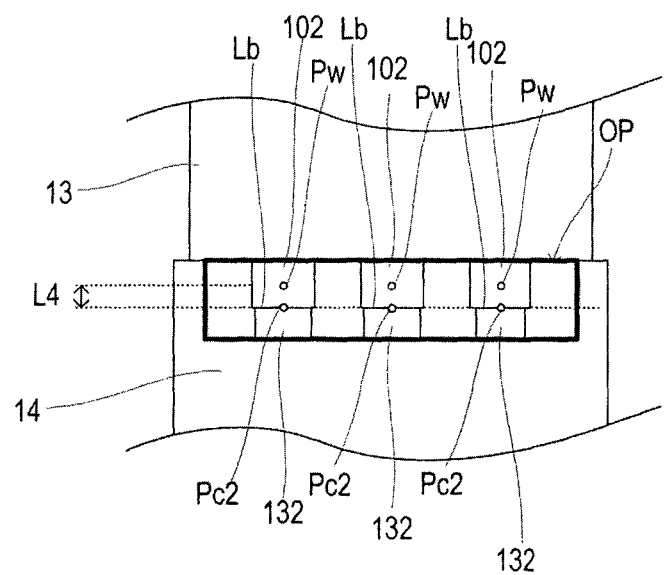
FIG. 15 is a diagram showing an opening OP and its periphery according to the other embodiment.

In the case of performing the boundary determination step at S45, as shown in FIG. 15, boundary lines Lb between the respective female connection portions 102 and the corresponding male connection portions 132 need to be exposed via the opening OP.

In the boundary determination step, first, the opening OP is photographed by a camera (not shown). Image data obtained by the camera photographing is inputted to a control unit of a laser welding apparatus (not shown). The control unit extracts the boundary lines Lb from the inputted image data through a known image recognition process. Then, the control unit detects the positions of the boundary lines Lb in an area photographed by the camera, on the basis of the extracted boundary lines Lb. Then, the control unit determines welding points Pw exposed via the opening OP, on the basis of the detected positions of the boundary lines Lb. For example, as shown in FIG. 15, a position apart upward from a midpoint Pc2 of each boundary line Lb by a predetermined distance L4 is determined as the position of each welding point Pw.

Specifically, the method for producing the gas sensor 1 includes the boundary determination step of: before welding the connection portion, photographing the opening OP from the outside of the insulating separator 12 to detect the boundary line Lb between each female connection portion 102 and the corresponding male connection portion 132; and determining the position of the connection portion on the basis of the result of the detection. Then, in the method for producing the gas sensor 1, in the welding step, welding is performed at the position determined in the boundary determination step. Thus, in the method for producing the gas sensor 1, the female connection portion 102 and the male connection portion 132 can be welded together with heat being accurately applied to the connection portion therebetween.

A function included in a single component in the aforementioned embodiment may be distributed to a plurality of components, or functions included in a plurality of components may be integrated in a single component. A part of the configuration of the aforementioned embodiment may be omitted. At least a part of the configuration of the aforementioned embodiment may be added to or replaced with another configuration in the embodiment. It should be noted that all aspects included in the technical idea specified by the description of the claims are included as embodiments of the present disclosure.

DESCRIPTION OF REFERENCE NUMERALS

1 . . . gas sensor
5 . . . detection element
12 . . . insulating separator
13 . . . front-side separator
14 . . . rear-side separator
33, 36 . . . electrode terminal portion
37 . . . lead wire 41 . . . metal terminal
43 . . . front-side terminal member
45 . . . rear-side terminal member
102 . . . female connection portion
113 . . . terminal contact portion
132 . . . male connection portion

The invention claimed is:

1. A metal terminal used for a gas sensor including: a sensor element having an electrode terminal portion configured to output a detection signal indicating a result of detection of a target gas to the outside; and a signal line forming a signal path for outputting the detection signal to the outside, the metal terminal comprising:
    a front-side terminal member that contacts the electrode terminal portion; and
    a rear-side terminal member that is connected to the signal line, wherein
    the metal terminal is electrically connected to the electrode terminal portion and the signal line for transmitting the detection signal from the electrode terminal portion to the signal line,
    the front-side terminal member includes a front-side connection portion via which the front-side terminal member is connected to the rear-side terminal member,
    the rear-side terminal member includes a rear-side connection portion via which the rear-side terminal member is connected to the front-side terminal member,
    the front-side connection portion is a female connection portion or a male connection portion,
    the rear-side connection portion is the male connection portion when the front-side connection portion is the female connection portion, and is the female connection portion when the front-side connection portion is the male connection portion,
    the female connection portion has an insertion port in which the male connection portion is inserted,
    the insertion port is formed in a shape that can prevent the insertion port and the male connection portion from coming into contact with each other when the male connection portion is inserted into the female connection portion through the insertion port,
    the female connection portion includes a terminal contact portion configured to bring the male connection portion and the female connection portion into contact with each other by pressing the male connection portion toward the female connection portion, when the male connection portion is inserted into the female connection portion,
    the female connection portion contains a cutout portion that is defined by an outer edge of the terminal contact portion, and
    the male connection portion and the female connection portion are welded together at a contact portion between the male connection portion and the female connection portion.

2. The metal terminal for the gas sensor according to claim 1, wherein
    at least two terminal contact portions are provided along a direction perpendicular to an insertion direction in which the male connection portion is inserted into the female connection portion.

3. The metal terminal for the gas sensor according to claim 1, wherein
    at least two terminal contact portions are provided along an insertion direction in which the male connection portion is inserted into the female connection portion.

4. The metal terminal for the gas sensor according to claim 1, wherein
    the front-side connection portion includes the terminal contact portion.

5. A gas sensor comprising:
    a sensor element having an electrode terminal portion configured to output a detection signal indicating a result of detection of a detection target gas to the outside;
    a metal terminal electrically connected to the electrode terminal portion of the sensor element; and
    a signal line electrically connected to the metal terminal, and forming a signal path for outputting the detection signal to the outside, wherein
    the metal terminal includes a front-side terminal member that contacts the electrode terminal portion, and a rear-side terminal member that is connected to the signal line,
    the front-side terminal member includes a front-side connection portion via which the front-side terminal member is connected to the rear-side terminal member,
    the rear-side terminal member includes a rear-side connection portion via which the rear-side terminal member is connected to the front-side terminal member,
    the front-side connection portion is a female connection portion or a male connection portion,
    the rear-side connection portion is the male connection portion when the front-side connection portion is the female connection portion, and is the female connection portion when the front-side connection portion is the male connection portion,
    the female connection portion has an insertion port in which the male connection portion is inserted,
    the insertion port is formed in a shape that can prevent the insertion port and the male connection portion from coming into contact with each other when the male connection portion is inserted into the female connection portion through the insertion port,
    the female connection portion includes a terminal contact portion configured to bring the male connection portion and the female connection portion into contact with each other by pressing the male connection portion toward the female connection portion, when the male connection portion is inserted into the female connection portion,
    the female connection portion contains a cutout portion that is defined by an outer edge of the terminal contact portion, and
    the male connection portion and the female connection portion are welded together at a contact portion between the male connection portion and the female connection portion.

6. The gas sensor according to claim 5, further comprising:
    a contact point at which the terminal contact portion is in contact with either the female connection portion or the male connection portion; and
    a welding point at which the female connection portion and the male connection portion are welded together, wherein
    the contact point and the welding point are located on the same plane perpendicular to an insertion direction in which the male connection portion is inserted into the female connection portion.

7. The gas sensor according to claim 5, wherein
at least two terminal contact portions are provided along an insertion direction in which the male connection portion is inserted into the female connection portion,
among the at least two terminal contact portions, one terminal contact portion is regarded as a first terminal contact portion, and one terminal contact portion other than the first terminal contact portion is regarded as a second terminal contact portion, and
a first contact point at which the first terminal contact portion is in contact with either the female connection portion or the male connection portion and a second contact point at which the second terminal contact portion is in contact with either the female connection portion or the male connection portion are located on opposite sides from each other with a welding plane therebetween, the welding plane being perpendicular to the insertion direction in which the male connection portion is inserted into the female connection portion, and passing a welding point at which the female connection portion and the male connection portion are welded together.

8. A metal terminal used for a gas sensor including: a sensor element having an electrode terminal portion configured to output a detection signal indicating a result of detection of a target gas to the outside; and a signal line forming a signal path for outputting the detection signal to the outside, the metal terminal comprising:
a front-side terminal member that contacts the electrode terminal portion; and
a rear-side terminal member that is connected to the signal line, wherein
the metal terminal is electrically connected to the electrode terminal portion and the signal line for transmitting the detection signal from the electrode terminal portion to the signal line,
the front-side terminal member includes a front-side connection portion via which the front-side terminal member is connected to the rear-side terminal member,
the rear-side terminal member includes a rear-side connection portion via which the rear-side terminal member is connected to the front-side terminal member,
the front-side connection portion is a female connection portion or a male connection portion,
the rear-side connection portion is the male connection portion when the front-side connection portion is the female connection portion, and is the female connection portion when the front-side connection portion is the male connection portion,
the female connection portion has an insertion port in which the male connection portion is inserted,
the insertion port is formed in a shape that can prevent the insertion port and the male connection portion from coming into contact with each other when the male connection portion is inserted into the female connection portion through the insertion port,
the male connection portion includes a terminal contact portion configured to bring the male connection portion and the female connection portion into contact with each other by pressing the male connection portion toward the female connection portion, when the male connection portion is inserted into the female connection portion, and
the terminal contact portion protrudes outward in a direction perpendicular to an axial direction of the gas sensor.

9. The metal terminal for the gas sensor according to claim 1, wherein the front-side connection portion is the female connection portion.

10. The metal terminal for the gas sensor according to claim 1, wherein the terminal contact portion is bent inward so that a diameter of the female connection portion decreases toward a front side of the gas sensor.

11. The metal terminal for the gas sensor according to claim 1, wherein at least portions of the male connection portion and the female connection portion are separated from each other when the male connection portion is inserted into the female connection portion through the insertion port.

* * * * *